(12) United States Patent
Bhaumik et al.

(10) Patent No.: US 9,414,761 B2
(45) Date of Patent: Aug. 16, 2016

(54) QRS COMPLEX IDENTIFICATION IN ELECTROCARDIOGRAM SIGNALS

(71) Applicant: INDIAN INSTITUTE OF TECHNOLOGY DELHI, Hauz Khas, New Delhi (IN)

(72) Inventors: Basabi Bhaumik, New Delhi (IN); Sanjeev Kumar Jain, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 0 days.

(21) Appl. No.: 14/573,037

(22) Filed: Dec. 17, 2014

(65) Prior Publication Data
US 2015/0342489 A1 Dec. 3, 2015

(30) Foreign Application Priority Data
Jun. 2, 2014 (IN) .......................... 1463/DEL/2014

(51) Int. Cl.
A61B 5/0472 (2006.01)
A61B 5/0452 (2006.01)
A61B 5/0456 (2006.01)
A61B 5/00 (2006.01)

(52) U.S. Cl.
CPC ............. A61B 5/0472 (2013.01); A61B 5/0452 (2013.01); A61B 5/0456 (2013.01); A61B 5/7225 (2013.01)

(58) Field of Classification Search
None
See application file for complete search history.

(56) References Cited

U.S. PATENT DOCUMENTS

| | | | | | |
|---|---|---|---|---|---|
| 3,577,983 A * | 5/1971 | Baessler | .............. | A61B 5/0452 600/515 |
| 4,896,677 A * | 1/1990 | Kaneko | ................ | A61B 5/0436 600/509 |
| 5,188,116 A * | 2/1993 | Pommrehn | .......... | A61B 5/0456 600/509 |
| 5,738,104 A * | 4/1998 | Lo | ...................... | A61B 5/02438 600/509 |
| 5,749,367 A * | 5/1998 | Gamlyn | ............... | A61B 5/0006 600/509 |
| 8,112,150 B2 * | 2/2012 | Naqvi | ................ | A61B 5/02233 607/5 |
| 8,145,310 B2 * | 3/2012 | Dong | ..................... | A61N 1/371 607/27 |
| 8,433,395 B1 * | 4/2013 | Brockway | ............ | A61B 5/7203 600/509 |
| 8,668,644 B2 * | 3/2014 | Ong | ...................... | G06F 19/345 600/301 |
| 8,855,752 B2 * | 10/2014 | Johnson | ............... | A61B 5/0472 600/509 |
| 2004/0228217 A1 * | 11/2004 | Szeto | ................. | A61B 5/02455 368/11 |
| 2004/0267148 A1 * | 12/2004 | Arand | .................. | A61B 5/0245 600/528 |
| 2006/0178591 A1 * | 8/2006 | Hempfling | ........... | A61B 5/0816 600/529 |
| 2011/0184297 A1 * | 7/2011 | Vitali | ................. | A61B 5/04017 600/509 |
| 2013/0109989 A1 * | 5/2013 | Busse | ................. | A61B 5/1102 600/527 |

* cited by examiner

Primary Examiner — Kennedy Schaetzle
(74) Attorney, Agent, or Firm — RatnerPrestia (57) ABSTRACT

The present subject matter relates to processing of Electrocardiogram (ECG) signals, and in particular, relates to identifying a QRS complex in an ECG signal. The method includes receiving, and filtering the ECG signal by passing through at least one of a first low-pass filter and a high-pass filter to obtain a filtered ECG signal. The filtered ECG signal is processed based on a moving average technique. Further, a search region is identified in the processed ECG signal, and a maximum amplitude peak is identified in a time interval of the filtered ECG signal that corresponds to a time span of the search region of the processed ECG signal. The maximum amplitude peak is an R peak of the QRS complex. Subsequently, a Q peak and an S peak of the QRS complex is identified based on the R peak.

17 Claims, 8 Drawing Sheets

QRS COMPLEX IDENTIFICATION IN ELECTROCARDIOGRAM SIGNALS

CROSS REFERENCE TO RELATED APPLICATIONS

This application claims priority to Indian Patent Application No. 1463/DEL/2014, filed Jun. 2, 2014, the contents of such application being incorporated herein by reference.

TECHNICAL FIELD

The present subject matter relates, in general, to processing of Electrocardiogram (ECG) signals and, particularly but not exclusively, to identification of QRS complexes in ECG signals.

BACKGROUND

As is generally understood, diseases related to heart and blood vessels are referred to as cardiovascular diseases. Cardiovascular diseases have emerged as a serious health concern across the globe. Various devices are known for monitoring activities of heart of an individual using which the cardiovascular diseases can be detected. The activity of the heart of an individual is generally monitored based on electrical signals, referred to as Electrocardiogram (ECG) signals, which are obtained by attaching an ECG detector to a body of the individual An ECG signal includes a "QRS complex" which may be identified and analyzed to determine the cardiovascular diseases.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

System(s) and method(s) for identifying QRS complexes in Electrocardiogram (ECG) signals for detecting cardiovascular diseases are described. Also, an apparatus for detection of cardiovascular diseases using QRS complexes in ECG signals is described.

As is generally known, activity of heart of an individual can be expressed as electrical signals, such as ECG signals, which can be analyzed for detection of cardiovascular diseases for the individual. Typically, an ECG signal includes a waveform comprising a P wave, a Q wave, an R wave, an S wave, and a T wave. The Q wave, the R wave and the S wave of the ECG signal collectively referred to as a "QRS complex". In particular, the P-wave of the ECG signal depicts a de-polarization of an atrium of the heart. The QRS complex and T wave depict a de-polarization and a re-polarization of ventricles of the heart, respectively. Generally, among the five waves, the R wave is considered to be the most prominent wave in the waveform of the ECG signal. As a result, time intervals between successive R waves of an ECG signal can be utilized for determining a heart rate, i.e., a rate of heart beat, of an individual.

Usually, QRS complexes play a significant role in the ECG analysis performed for detection of cardiovascular diseases, and therefore, their accurate identification is equally relevant. Conventionally, the identification of QRS complexes involves passing an ECG signal through a band-pass filter in order to remove noise from the ECG signal. The band-pass filter, used conventionally, has a band-pass frequency range of 5 Hz to 11 Hz. However, with such a band-pass frequency range, a Q wave and an S wave of a QRS complex of the ECG signal may get distorted and consequently, may pose a difficulty in the identification of the QRS complex. In case the Q wave and the S wave are not identified or inaccurately identified, various parameters associated with the QRS complex may not be determined, and consequently, an accuracy of detection of cardiovascular diseases may be compromised.

Following the passage of the ECG signal through the filters, a moving average technique may be utilized for further processing a filtered ECG signal. In accordance with the conventional moving average technique, a moving average for the filtered ECG signal may be computed on the basis of past or historic ECG signals. Therefore, in order to compute the moving average, a large amount of past or historical ECG signals may have to be stored in a memory or a database for reference. Such large amount of data may need a large memory or database for storage and may also adversely affect the computation speed during the ECG analysis for detection of cardiovascular diseases. In addition, providing large memory or database in a conventional disease detection device, functioning based on ECG signals, may result into a significant increase in weight, size, and cost of the disease detection device.

In continuation with the computation of the moving average, the conventional techniques utilize adaptive thresholds for identification of the QRS complex. However, the utilization of the adaptive thresholds may lead to heavy computations, and consequently, may end up slowing down the computation speed of the overall analysis. Further, an initial threshold, among the adaptive thresholds, is usually patient specific. However, the conventional techniques utilize a standard set of parameters for defining the initial threshold. Since the initial threshold is defined using the standard set of parameters and is not patient-specific, an error in the identification of the QRS complex is possible.

Further, in some cases, a peak of the QRS complex may not be identified during the ECG analysis. In such cases, conventionally, a search back operation may be performed using the past or historical ECG signals, in order to find the missing peaks. The search back operation usually demands a large memory for execution, and therefore, may result into further slowing down the computation speed of the ECG analysis.

Further, a variety of disease detection devices may be utilized for recording the ECG signals and subsequently, performing the operations of ECG analysis for the detection of cardiovascular diseases. Usually, micro-controllers are utilized for facilitating operations of such devices for detection of cardiovascular diseases. However, the micro-controllers have substantially large power consumptions which adversely affect the efficiency of the conventional disease detection devices. In addition, use of microcontrollers may increase the size and weight of the disease detection device, and therefore, may pose a threat to portability of the disease detection devices.

Moreover, as mentioned earlier, conventional techniques do not allow identification of a Q wave and an S wave of a QRS complex. Consequently, parameters associated with identification of the Q wave and the S wave cannot be utilized for detection of cardiovascular diseases. Therefore, the disease detection devices utilizing such conventional techniques may be capable of detecting a single disease based on an R peak of an R wave of the QRS complex. As would be gathered, the conventional techniques offer a fragmented, inefficient, expensive and complex proposition for identification of QRS complexes for detecting cardiovascular diseases.

According to the present subject matter, systems and methods for identifying a QRS complex in an Electrocardiogram (ECG) signal is disclosed. In addition, an apparatus, implementing the systems and the methods of the present subject matter, for detection of cardiovascular diseases using QRS complex in ECG signals is disclosed.

In one implementation, the ECG signal, indicative of an electrical activity of heart of an individual, may be captured by an ECG recorder. The ECG signal, captured by the ECG recorder, may be filtered by passing the ECG signal through at least one of a first low-pass filter and a high-pass filter to obtain a filtered ECG signal. In one implementation, the first low-pass filter may have a cut-off frequency of 40 Hz, and the high-pass filter may have a cut-off frequency of 1.5 Hz.

The filtered ECG signal may further be processed, based on a moving average technique for ECG signals, for obtaining a processed ECG signal. In one implementation, the processing of the filtered ECG signal may include one or more sub-steps. For example, the filtered ECG signal may be squared to obtain a squared filtered ECG signal. Then, peaks of the squared filtered ECG signal may be captured, and an envelope ECG signal that conforms the captured peaks may be generated. Following the generation of the envelope ECG signal, a moving average ECG signal may be determined based on a moving average of sample points associated with the envelope ECG signal, where a sample point is indicative of amplitude of the envelope ECG signal at a time instance. In one implementation, the moving average ECG signal may further be filtered to obtain the processed ECG signal, by passing the moving average ECG signal through a second low-pass filter. In one example, the second low-pass filter may have a cut-off frequency of 8 Hz.

After generating the processed ECG signal, a search region may be identified in the processed ECG signal. The search region is indicative of a time span between two consecutive peaks of the processed ECG signal. Subsequently, a maximum amplitude peak may be identified in a time interval of the filtered ECG signal that corresponds to the time span of the search region of the processed ECG signal. In one implementation, the maximum amplitude peak is an R peak of an R wave of the QRS complex. Continuing with the present implementation, a Q peak of a Q wave, and an S peak of an S wave, of the QRS complex may be identified based on the R peak of the R wave.

As mentioned previously, at various stages of the analysis, the ECG signal may be passed through filters in order to remove noise and therefore, to make the ECG signal clearer. The present subject matter involves application of low-pass filters and high-pass filters with cut-off frequencies which would not distort the Q wave and the S wave of the QRS complex of the ECG signal. As a result, the QRS complex and various parameters associated with the QRS complex can be determined in an accurate manner. This would eventually assist in an accurate detection of the cardiovascular diseases. Also, as the complete QRS complex is identified, the system is capable of detecting multiple cardiovascular diseases.

Further, in accordance with the present subject matter, the moving average of the envelope ECG signal is determined in real time, and past digitized ECG signals may not be utilized for computation of the moving average. Therefore, the past or historical ECG samples may not have to be stored in a memory or a database. As a result, a size and capacity of the memory or the database can be reduced. Further, in accordance with the present subject matter, in case of finding missed-out peaks of QRS complex, a forward search may be performed for identifying the peaks of the QRS complex instead of a search back operation as performed conventionally. Since the search back operation need not be performed, the past or historical ECG signals may not be stored in the memory. This may assist in reducing the size and the capacity of the memory or the database, and may also assist in enhancing the processing speed of the system or the apparatus. Therefore, time for performing the analysis of ECG signals may be reduced. In addition, the reduction in size of the memory or the database may also lead to a reduction in an overall size and the cost of an apparatus implementing the system and the method of the present subject matter.

Further, the present subject matter does not employ a micro-controller for facilitating operations of the system. Instead, in one implementation, an Application Specific Integrated Chip (ASIC) may be utilized for implementing the system. The ASIC may utilize digital circuits, e.g., combinational and sequential circuits, for implementing the system. Therefore, the system, or the apparatus implementing the system, may not consume large power, and consequently, may be implemented as a low power portable system or apparatus.

The method, the system, and the apparatus, of the present subject matter provide a comprehensive approach for a fast, accurate, and inexpensive identification of the QRS complex in ECG signals, and therefore, detection of the cardiovascular diseases based on the QRS complex.

These and other advantages of the present subject matter would be described in greater detail in conjunction with the following figures. While aspects of described system(s) and method(s) for identifying a QRS complex in an Electrocardiogram (ECG) signal can be implemented in any number of different computing systems, environments, and/or configurations, the embodiments are described in the context of the following exemplary system(s).

Figure 1:
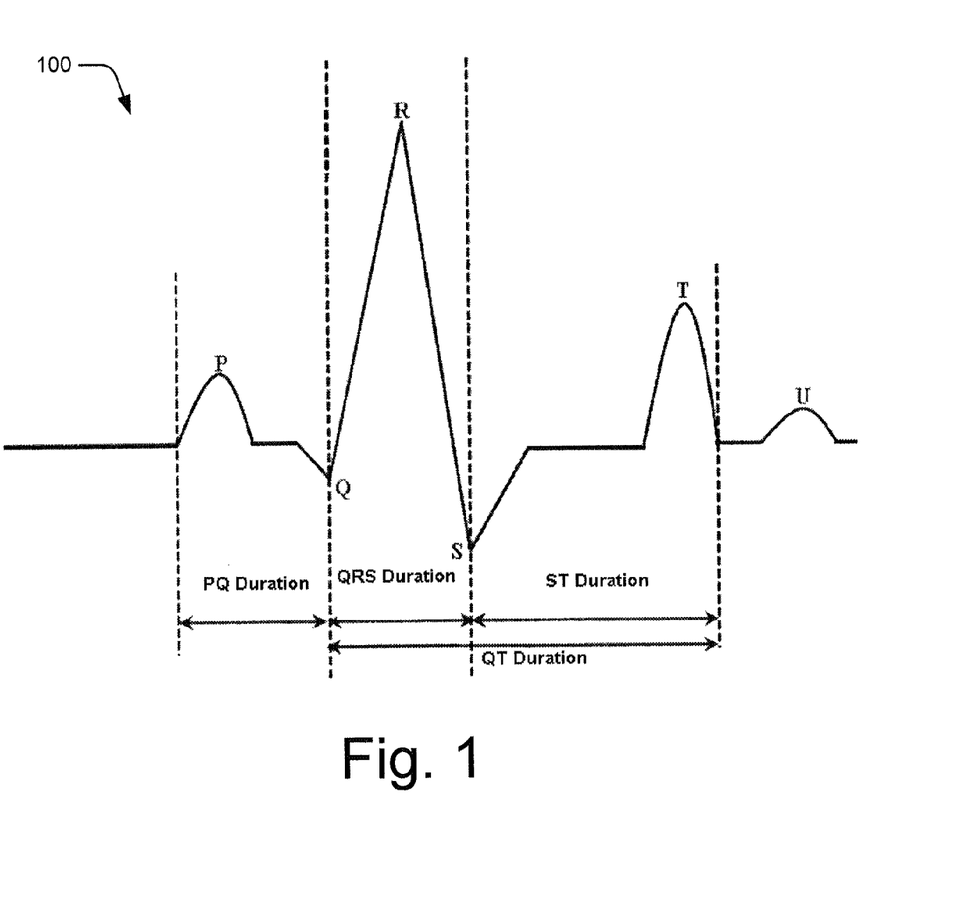
FIG. 1 illustrates a typical Electrocardiogram (ECG) signal depicting electrical activity of heart of an individual.

FIG. 1 illustrates a typical Electrocardiogram (ECG) signal 100 depicting an electrical activity of heart of an individual. As is generally understood, the ECG signal 100 is indicative of an electrical activity of heart of an individual, which may be picked up by an ECG recording device attached to the individual. As is shown in FIG. 1, the ECG signal 100 follows a pattern, referred to as a PQRST pattern. The PQRST pattern includes a P wave, a Q wave, an R wave, an S wave, and a T wave. In particular, the P wave of the ECG signal 100 represents atria contraction of the heart. Further, a QRS complex, consisting of the Q wave, the R wave and the S wave, represents ventricular contraction of the heart. As can be seen, a first negative deflection and a first positive deflection of the QRS complex is represented by the Q wave and the R wave, respectively. On the other hand, a first negative deflection after the R wave is represented by the S wave.

Further, the P wave and the QRS complex represent an atria depolarization and a ventricular depolarization, respectively. Once depolarized, ventricular cells of the heart return to their initial or resting state. The process of returning of the ventricular cells to the resting state, after depolarization, is known as re-polarization. An atria re-polarization occurs after the P wave, and is hidden in the QRS complex. Similarly, a ventricular re-polarization is represented by the T wave.

Figure 2:
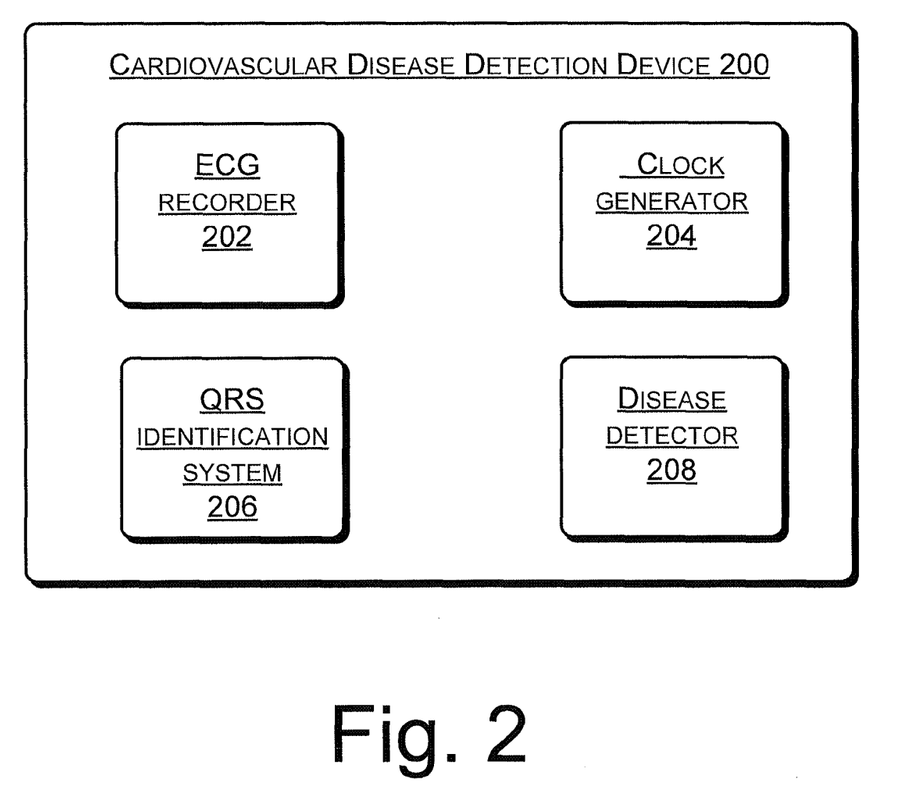
FIG. 2 illustrates a cardiovascular diseases detection apparatus for detection of cardiovascular diseases using QRS complexes in Electrocardiogram (ECG) Signals, in accordance with an embodiment of the present subject matter.

FIG. 2 illustrates a cardiovascular diseases detection apparatus 200 for detection of cardiovascular diseases using QRS complexes in Electrocardiogram (ECG) signals, in accordance with an embodiment of the present subject matter. The cardiovascular diseases detection apparatus 200 includes an ECG recorder 202, a clock generator 204, a QRS identification system 206 and a disease detector 208. The ECG recorder 202 may be a sensor utilized for detecting and recording electrical impulses generated by polarization and depolarization of cardiac tissues of the heart of an individual. The ECG recorder 202 may translate the electrical impulses into ECG signals, which can further be used to determine parameters associated with heartbeats, e.g., rate and regularity of heartbeats, size and position of chambers, any damage to the heart, and effects of drugs or devices used to regulate the heart, such as a pacemaker.

In one implementation, the clock generator 204 may be understood as a circuit for generating timing signals for synchronizing operations of devices or systems, in the form of electronic circuits, coupled with the clock generator 204. For example, in the cardiovascular diseases detection apparatus 200, the clock generator 204 may assist in synchronizing operations of the ECG recorder 202, the QRS identification system 206 and the disease detector 208. The construction and the operation of the clock generator 204 are explained in detail with reference to FIG. 6 and FIG. 7.

In one implementation, the QRS identification system 206, hereinafter referred to as the system 206, may analyze ECG signals, captured by the ECG recorder 202, for identification of QRS complexes. Initially, the QRS identification system 206 may receive an ECG signal from the ECG recorder 202. Upon receiving, the system 206 may filter and process the ECG signal for obtaining a processed ECG signal. In one implementation, the system 206 may process the ECG signal based on a moving average technique for ECG signals. Once the processed ECG signal is obtained, the system 206 may further identify a search region in the processed ECG signal. Based on the search region, the system 206 may identify an R peak of an R wave, and subsequently, a Q peak of a Q wave and an S peak of an S wave, of a QRS complex of the ECG signal. The construction and the operation of the system 206 for identification of a QRS complex from the ECG signal is explained in detail with reference to FIG. 3, FIG. 4, and FIG. 5.

Following the identification of the QRS complex, the system 206 may transmit data or information pertaining to the identified QRS complex to the disease detector 208. Based on the received data or information, the disease detector 208 may then detect a cardiovascular disease associated with the individual. In one implementation, the disease detector 208 may detect one or more of cardiovascular diseases, such as Bradycardia, Tachycardia, Left bundle branch block, Right bundle branch block, Intra-ventricular conduction delay, Left ventricular hypertrophy and Right ventricular hypertrophy.

Figure 3:
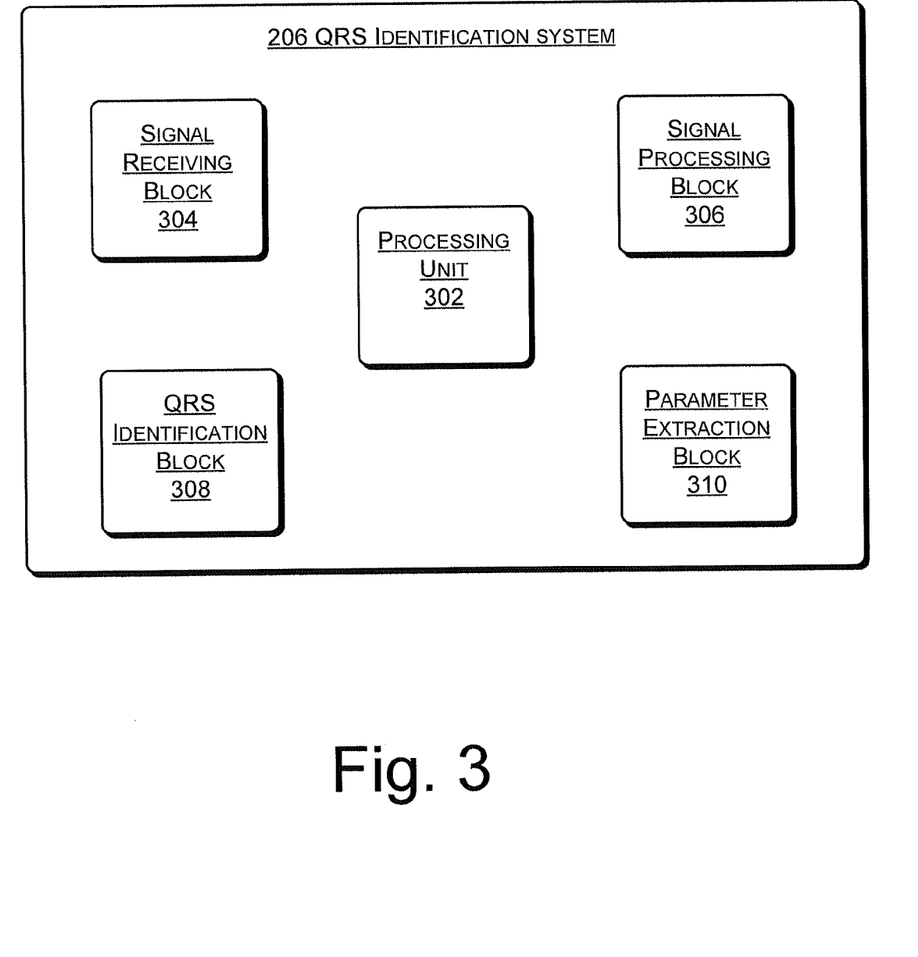
FIG. 3 illustrates a QRS identification system of the cardiovascular diseases detection apparatus, in accordance with an embodiment of the present subject matter.

FIG. 3 illustrates the QRS identification system 206 of the cardiovascular disease detection apparatus 200, in accordance with an embodiment of the present subject matter. The system 206 may include, but is not limited to, a processing unit 302, a signal receiving block 304, a signal processing block 306, a QRS identification block 308 and a parameter extraction block 310. In one implementation, the signal receiving block 304, the signal processing block 306, the QRS identification block 308 and the parameter extraction block 310 may be coupled with the processing unit 302.

In one implementation, the processing unit 302 may be implemented as one or more microprocessors, microcomputers, digital signal processors, central processing units, state machines, logic circuitries, and/or any devices that manipulate signals based on operational instructions.

In one implementation, the signal receiving block 304 may receive an ECG signal, from the ECG recorder 202. In one example, the ECG signal may have a frequency of 1000 Hz. Upon receiving the ECG signal, the signal receiving block 304 may down-sample the ECG signal. As is generally known, down-sampling is a process utilized for reducing a sampling rate of a signal, and therefore, for reducing the size of data associated with the signal. In one implementation, the signal receiving block 304 may down-sample the ECG signal based on a predefined reduction factor. In an example, the predefined reduction rate may be 4, with which the ECG signal of a frequency of 1000 Hz may be down-sampled to an ECG signal of a frequency of 250 Hz. The predefined reduction factor may be selected depending on the frequency of the ECG signal received from the ECG recorder 202 and depending on the frequency of the down-sampled ECG signal.

Following the down-sampling of the ECG signal, the signal receiving block 304 may pass the down-sampled ECG signal through at least one of a first low-pass filter and a high-pass filter, to obtain a filtered ECG signal. The down-sampled ECG signal is passed through at least one of the first low-pass filter and the high-pass filter in order to remove noise from the down-sampled ECG signal. In an example, where the down-sampled ECG signal has the frequency of 250 Hz, the first low-pass filter may have a cut-off frequency of 40 Hz, and the high-pass filter may have a cut-off frequency of 1.5 Hz. With this, the filtered ECG signal may have a frequency in a range of 1.5 Hz-40 Hz. In one implementation, the first low-pass filter may have a cut-off frequency within a range of 15 Hz-40 Hz. Similarly, the high-pass filter may have a cut-off frequency of 0.5 Hz-5 Hz.

The cut-off frequencies of the first low-pass filter and the high-pass filter may vary based on a frequency of the down-sampled ECG signal. The cut-off frequencies of the first low-pass filter and the high-pass filter are selected in such a manner that a Q wave and an S wave of a QRS complex in the resultant filtered ECG signal may not get distorted and can be identified. In one implementation, the first low-pass filter and the high-pass filter are integer type filters.

Further, the signal receiving block 304 may provide the filtered ECG signal to the signal processing block 306. The signal processing block 306 may perform a square operation on the filtered ECG signal. As is generally known, in accordance with the square operation, the signal processing block 306 may multiply the filtered ECG signal with itself, and therefore, a squared filtered ECG signal may be obtained. The signal processing block 306 may capture peaks of the squared filtered ECG signal and generate an envelope ECG signal. The envelope ECG signal is a signal that envelops the peaks of the filtered ECG signal.

In continuation with the generation of the envelope ECG signal, the signal processing block 306 may determine a moving average ECG signal, based on a moving average of sample points associated with the envelope ECG signal. As is generally known, a sample point is indicative of amplitude of the envelope ECG signal at a time instance. In one implementation, the signal processing block 306 may divide the envelope ECG signal into sample points. The signal processing block 306 may divide the envelope ECG signal into multiple sections, where each section includes a predefined number of sample points separated based on a predefined sampling rate. For example, each section of the envelope ECG signal may include 32 sample points. In one implementation, the predefined number of sample points may be selected based on an optimizing gain of the moving average signal. In one example with a sampling frequency being 250 Hz, each sample point may be separated from an adjacent sample point by a time duration of 4 milliseconds. The signal processing block 306 may further evaluate, for each section of the envelope ECG signal, an average of the sample points in order to determine the moving average ECG signal. Since, the moving average ECG signal is determined based on the ECG signal captured in real-time the past ECG signals may not be utilized for the determination of the moving average ECG signal.

In one implementation, the signal processing block 306 may further pass the moving average ECG signal through a second low-pass filter, for obtaining a processed ECG signal. In one example, where the filtered ECG signal may have the frequency range of 1.5 Hz-40 Hz, the second low-pass filter may have a cut-off frequency of 8 Hz. In one implementation, the second low-pass filter may have a cut-off frequency within a range of 8 Hz-16 Hz. The signal processing block 306 may pass the moving average ECG signal through the second low-pass filter in order to improve a signal to noise ratio of the processed ECG signal.

Figure 4:
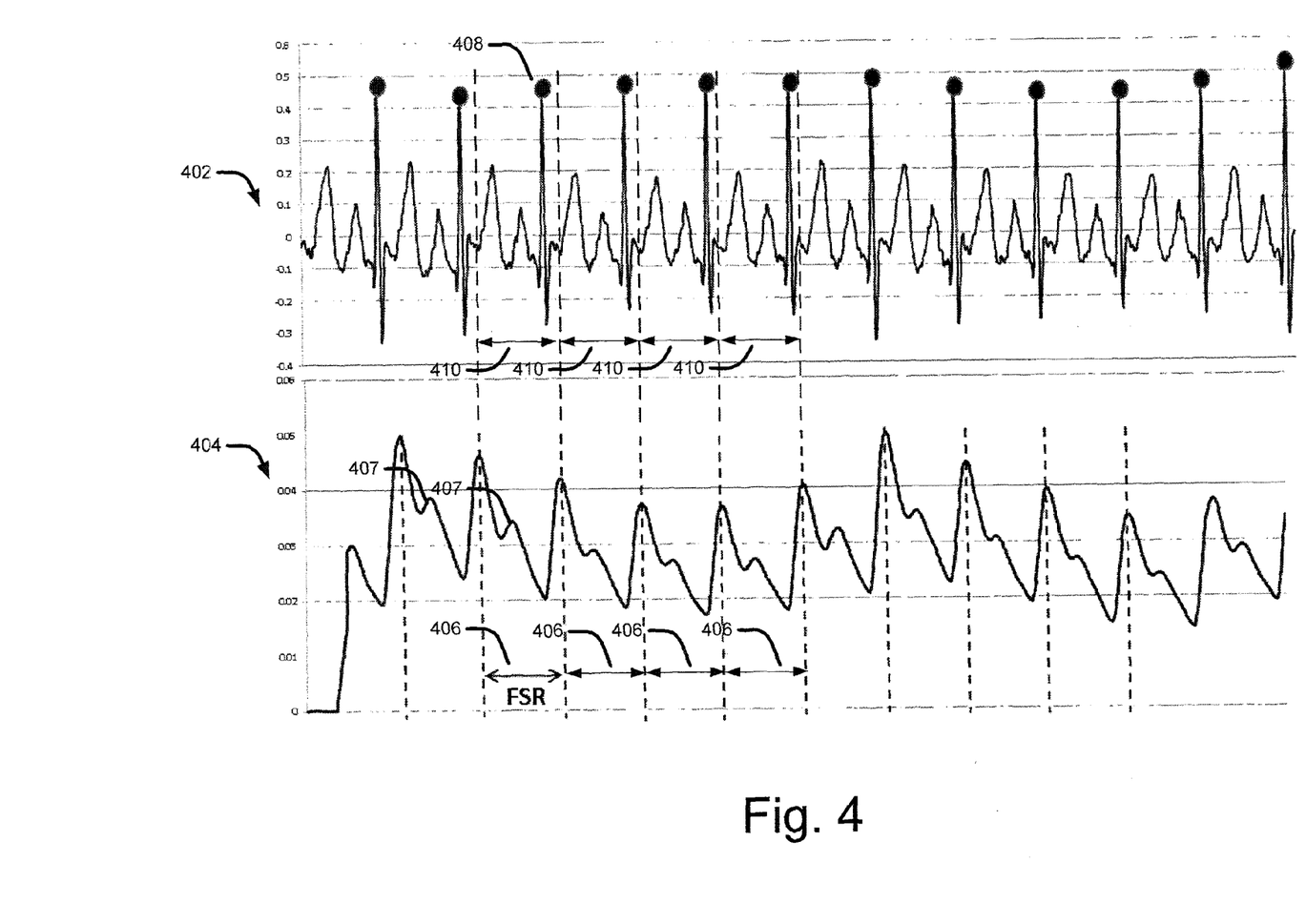
FIG. 4 illustrates a filtered ECG signal and a processed ECG signal for identification of an R peak of an R wave of a QRS complex in an ECG signal, in accordance with an embodiment of the present subject matter.

Once the processed ECG signal is obtained, the QRS identification block 308 may identify a search region in the processed ECG signal, based on which an R peak of an R wave of a QRS complex in the ECG signal may be identified. FIG. 4 is provided that illustrates the filtered ECG signal and the processed ECG signal for identification of an R peak of an R wave of a QRS complex in the ECG signal, in accordance with an embodiment of the present subject matter. In FIG. 4, the filtered ECG signal and the processed ECG signal are referenced by numerals 402 and 404, respectively. The filtered ECG signal 402 and the processed ECG signal 404 are depicted on a graph with amplitude plotted on Y axis, and time plotted on X axis. In one implementation, the QRS identification block 308 may identify a search region 406 between two consecutive peaks in the processed ECG signal 404. Thus, the search region 406 is indicative of a time span between the two consecutive peaks of the processed ECG signal 404. The QRS identification block 308 may identify similar search regions 406 between each pair of consecutive peaks in the processed ECG signal 404.

In one implementation, the processed ECG signal 404 may include T peaks 407 of T waves. However, the QRS identification block 308 may not consider the T peaks 407 for the identification of the search regions 406. In order to identify the peaks to be considered for identifying the search regions 406, the QRS identification block 308 may utilize a peak threshold. For example, the QRS identification block 308 may consider peaks, in the processed ECG signal 404, with amplitude above the peak threshold, for the identification of the search regions 406. Further, each of the T peaks 407 may have amplitude below the peak threshold and therefore, the T peaks 407 may not be considered for the identification of the search regions 406. Further, the QRS identification block 308 may determine the peak threshold for a predefined number of search regions 406, based on the peaks occurred in a previous set of predefined number of search regions 406. In one example with the predefined number of search regions 406 being 4, the QRS identification block 308 may determine a peak threshold for four search regions 406, based on peaks occurred in a previous set of four search regions 406. In one example, QRS identification block 308 may not consider an initial section, for a predefined time period, of the processed ECG signal 404 for identification of the search regions 406.

Further, the QRS identification block 308 may update the peak threshold after the predefined number of search regions 406 for obtaining an updated peak threshold, which would be utilized for detection of peaks, in the filtered ECG signal 402, for the identification of a next set of predefined number of search regions 406. Continuing with the present example, after the four search regions 406, the QRS identification block 308 may update the peak threshold, based on the peaks occurred in the four search regions 406, which would be utilized for detection of peaks for identification of a next set of four search regions 406.

Upon identifying a search region 406 in the processed ECG signal 404, the QRS identification block 308 may detect a maximum amplitude peak 408 in a time interval 410 of the filtered ECG signal 402 that corresponds to the time span of the search region 406 of the processed ECG signal 404. In one implementation, the maximum amplitude peak 408 can be detected based on amplitudes of the filtered ECG signal 402 at various time instances within the search region 406. The maximum amplitude peak 408 is the R peak of the R wave of the QRS complex.

Figure 5:
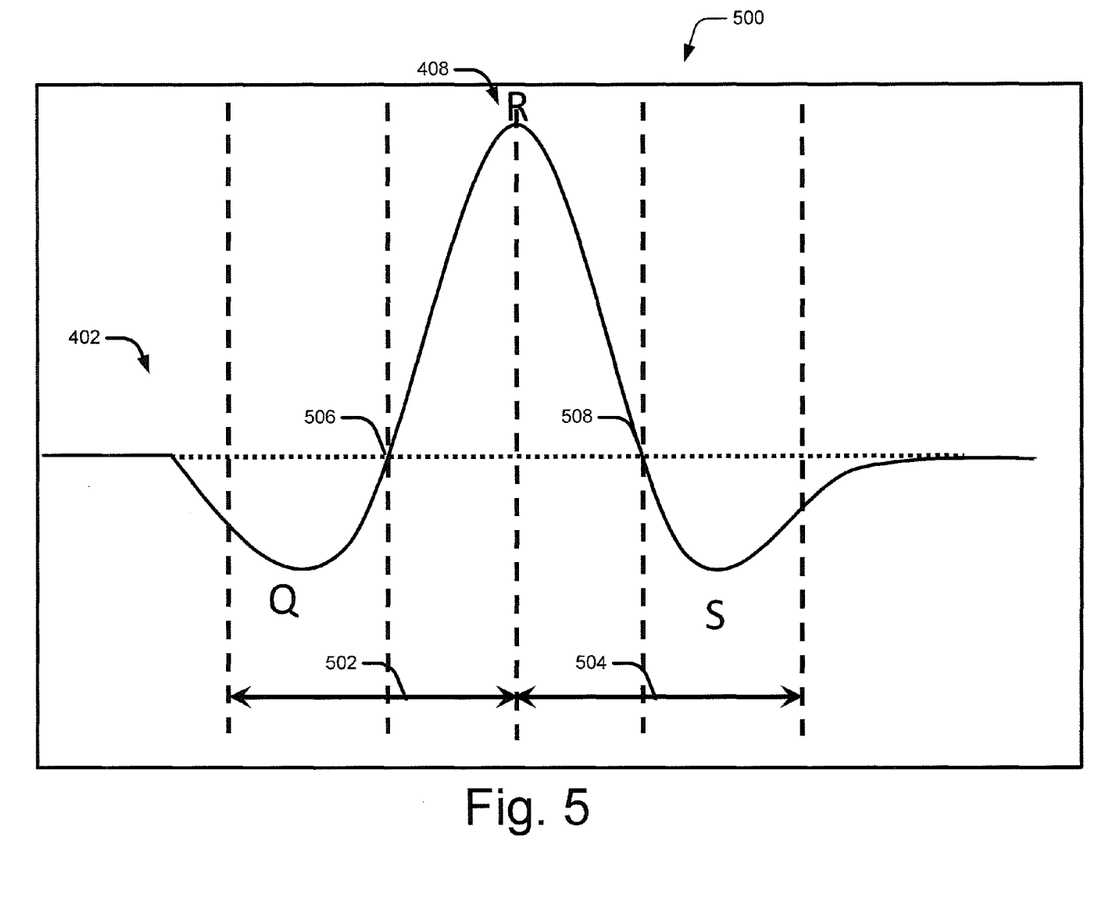
FIG. 5 illustrates the filtered ECG signal about the R peak identified in the filtered ECG signal for identification of a QRS complex, in accordance with an embodiment of the present subject matter.

The further analysis of the filtered ECG signal for identification of the QRS complex based on the R peak of the R wave is described with reference to FIG. 5. FIG. 5 illustrates the filtered ECG signal 402 about the R peak identified in the filtered ECG signal 402 for identification of a QRS complex 500, in accordance with an embodiment of the present subject matter. With regard to FIG. 5, the QRS identification block 308 may identify a first sub-search region 502 and a second sub-search region 504 of the filtered ECG signal 402. In one implementation, the first sub-search region 502 is indicative of a region comprising a predefined set of sample points of the filtered ECG signal 402, before a time instance of the R peak 408. A sample point is indicative of a location of the filtered ECG signal 402 on the shown time-amplitude curve. In one implementation, the QRS identification block 308 may utilize the first sub-search region for identification of the Q peak of the Q wave of the QRS complex 500. On the other hand, the second sub-search region 504 is indicative of a region comprising a predefined set of sample points of the filtered ECG signal 402, after the time instance of the R peak 408. In one implementation, QRS identification block 308 may utilize the second sub-search region 504 for identification of the S peak of the S wave of the QRS complex 500. Further, in one example, the predefined set of sample points may include 20 sample points. In an example with the sampling rate being 250, each of the predefined set of sample points may be 4 milliseconds apart from the adjacent sample point.

Upon identifying the first sub-search region 502 and the second sub-search region 504, the QRS identification block 308 may identify the Q wave and the S wave, based on predefined identification criteria. In one implementation, the QRS identification block 308 may identify the Q wave and the S wave, based on a first predefined identification criterion. In accordance with the first predefined identification criterion, the QRS identification block 308 may determine, within the first sub-search region 502, a segment of the filtered ECG signal 402, which includes a predefined number of consecutive sample points with slope greater than a predefined slope threshold. In the present implementation, in such a segment, one of the predefined number of consecutive sample points is identified as a first peak point. The first peak point in the first sub-search region 502 is the Q peak of the Q wave of the QRS complex 500. Similarly, QRS identification block 308 may determine, within the second sub-search region 502, a segment of the filtered ECG signal 402, where a slope of a predefined number of consecutive sample points is greater than a predefined slope threshold. In such a segment, one of the predefined number of consecutive sample points may be determined as a first peak point. The first peak point in the second sub-search region 502 is identified as the S peak of the S wave of the QRS complex 500. In one example, the predefined number of consecutive sample points may be 3.

In one implementation, the QRS identification block 308 may determine the predefined slope threshold utilizing the first search region 502 and the second search region 504. In one example, the QRS identification block 308 may evaluate a maximum slope, hereinafter referred to as positive maximum slope, of positive sample points of the filtered ECG signal 402. Similarly, a maximum slope, hereinafter referred to as negative maximum slope, of negative sample points of filtered ECG signal 402 may also be evaluated. Thereafter, the QRS identification block 308 may consider minimum of the positive maximum slope and the negative maximum slope, and may divide the minimum by eight to obtain the predefined slope threshold. The predefined slope threshold may be determined for each set of predefined number of search regions 406.

In an alternative implementation, the QRS identification block 308 may identify the Q wave and the S wave based on a second predefined identification criterion. In accordance with the second predefined identification criterion, the QRS identification block 308 may determine, within the first sub-search region 502, a second peak point that corresponds to a peak of the filtered ECG signal 402 in the first sub-search region 502. The second peak point in the first sub-search region 502 is the Q peak of the Q wave of the QRS complex 500. Similarly, the QRS identification block 308 may determine, within the second sub-search region 502, a second peak point that corresponds to a peak of the filtered ECG signal 402 in the second sub-search region 502. In one implementation, the second peak point may be determined based on three-point derivatives for the filtered ECG signal 402. In one example, as a result of evaluation of three-point derivatives for the filtered ECG signal 402, a slope signal may be obtained. In such an example, the second peak point may refer to a zero crossing point of the slope signal. The second peak point in the second sub-search region 502 is the S peak of the S wave of the QRS complex 500.

In one implementation, the QRS identification block 308 may identify the Q peak of the Q wave before a first zero crossing point 506 of the first sub-search region 502. Similarly, the QRS identification block 308 may identify the S peak of the S wave after a second zero crossing point 508 of the second sub-search region 504.

In one implementation, for the identification of the Q wave, the QRS identification block 308 may determine the first peak point and the second peak point based on the first predefined identification criterion and the second predefined identification criterion, respectively. In such an implementation, the QRS identification block 308 may identify the Q peak of the Q wave of the QRS complex 500 as one of the first peak point and the second peak point, based on a distance of the first peak point and the second peak point from the R peak of the R wave. In one example, the Q peak may be identified as one of the first peak point and the second peak point which is closer to the R peak of the R wave of the QRS complex 500. Similarly, for the identification of the S wave, one of the first peak point and the second peak point which is closer to the R peak may be considered as the S peak of the S wave of the QRS complex 500.

In one implementation, the QRS identification block 308 may not be able to identify the Q peak of the Q wave and the S peak of the S wave based on the abovementioned predefined identification criteria. This may happen, for example, when the first sub-search region 502 and the second sub-search region 504 in the filtered ECG signal for an individual are flat. In such a case, the first sub-search region 502 and the second sub-search region may not have any peak, and the QRS identification block 308 may utilize a third predefined identification criterion to identify the Q peak of the Q wave and the S peak of the S wave. In accordance with the third predefined identification criterion, the QRS identification block 308 may identify third peak points that correspond to minimum values in the first sub-search region 502 and in the second sub-search region 504. The Q peak of the Q wave is then identified as the third peak point in the first sub-search region 502, and the S peak of the S wave is then identified as the third peak point in the second sub-search region 504.

In continuation with the identification of the QRS complex 500, the parameter extraction block 310 of the QRS identification system 206 may extract parameters associated with the QRS complex 500. The parameters associated with the QRS complex 500 may include, but are not limited to a time duration between two consecutive R peaks, details pertaining to the R wave, details pertaining to the Q wave, details pertaining to the S wave, a time duration of the QRS complex 500. The parameter extraction block 310 may further transmit the parameters to the disease detector 208, which may utilize the parameters for detection of cardiovascular diseases.

Figure 6:
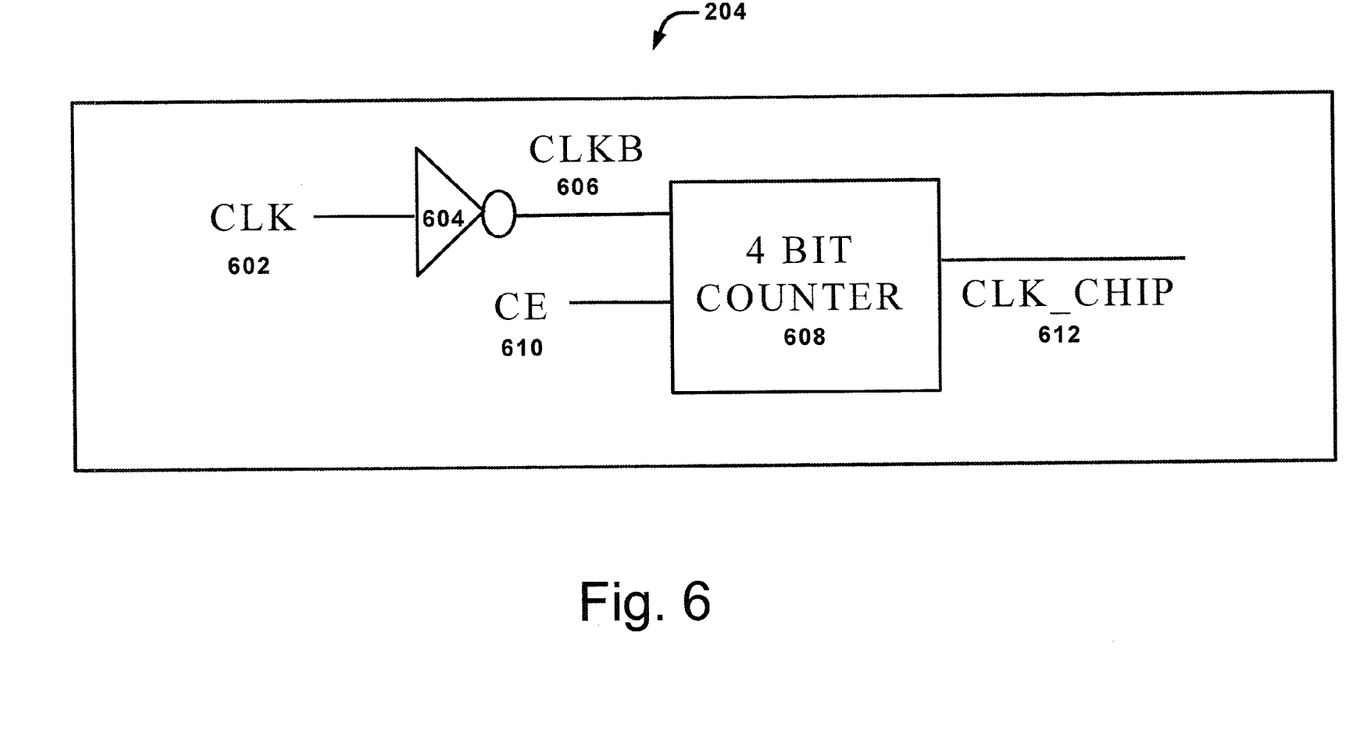
FIG. 6 illustrates a clock generator of the cardiovascular diseases detection apparatus, in accordance with an embodiment of the present subject matter.

FIG. 6 illustrates the clock generator 204 of the cardiovascular disease detection apparatus 200, in accordance with an embodiment of the present subject matter. FIG. 6 is an example implementation of the present subject matter, and therefore, should not be construed as limiting.

As shown in FIG. 6, an external clock signal CLK 602 may be passed through a device 604 for generating the inverted clock signal CLKB 606. The device 604 can be implemented in the clock generator 204 using any combinational logic circuit. In an implementation, the device 604 may be an inverter. An incoming ECG signal data may be processed at a falling edge and a rising edge of the external clock CLK 602 and the inverted clock CLKB 606, respectively. This would eliminate time required for setup, and hold time violation for receiving data into the clock generator 204.

In one example, the ECG signal, received from the ECG recorder 202, may be of 16 bit. In order to capture 16 bit parallel ECG data, the clock generator 204 may include a counter 608. Further, a chip enable signal CE 610 may be provided to the counter 608. The chip enable signal CE 610 may be set to "high" or "1" for resetting at least the clock generator 204. In the present example, the counter 608 may be a 4-bit counter that may be utilized for capturing the 16 bit parallel ECG data. The bits of the counter 608 may vary based on data bits of the ECG signal. In one implementation, the counter 608 may be implemented in the clock generator 204 by using combinational and sequential logic circuits. Further, the counter 608 may be triggered at a negative edge of the external clock signal 602. In one implementation, the clock generator 204 may include an internal generated clock signal CLK_CHIP 612 available at an output pin of the clock generator 204. In one implementation, the internal generated clock signal CLK_CHIP 612 may be utilized in order to obtain parallel outputs for ECG data. In one example, the internal generated clock signal CLK_CHIP 612 is a fraction of the external clock signal 602. For example, the internal clock signal CLK_CHIP 612 is a ⅟16 of the external clock signal 602. Therefore, the utilization of the internal generated clock signal CLK_CHIP 612 may assist in reducing power dissipation.

Figure 7:
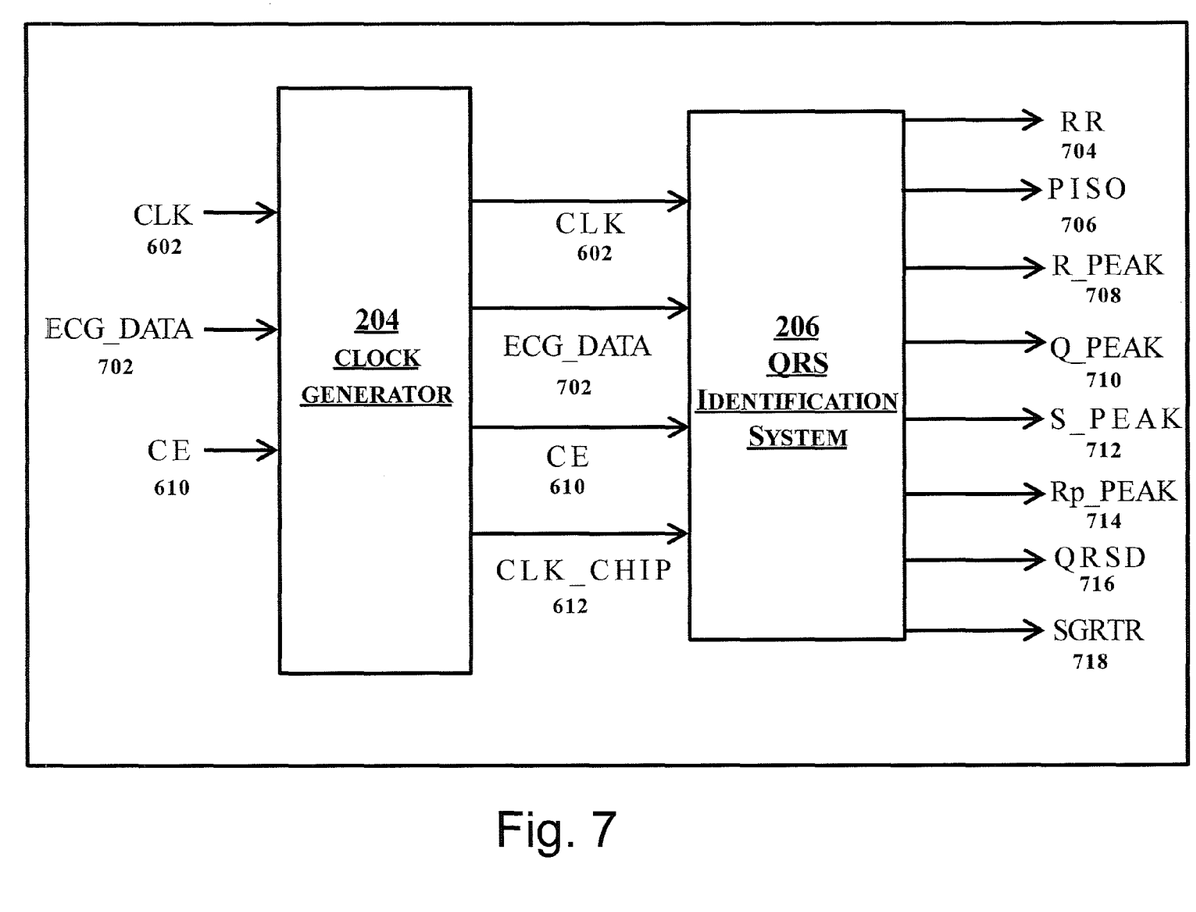
FIG. 7 illustrates coupling between a clock generator and a QRS identification system of the cardiovascular disease detection apparatus, in accordance with an embodiment of the present subject matter.

FIG. 7 illustrates coupling between the clock generator 204 and the QRS identification system 206 of the cardiovascular disease detection apparatus 200, in accordance with an embodiment of the present subject matter.

In one example, the combination of the clock generator 204 and the QRS identification system 206 in the cardiovascular disease detection apparatus 200 may include a number of input pins and output pins. The number of input pins and output pins may vary based on the application of the cardiovascular disease detection apparatus 200. The input pins include pins through which signals are provided to the clock generator 204 for operating the QRS identification system 206. The output pins include pins through which signals are drawn out from the QRS identification system 206 for the purpose of detection of cardiovascular diseases.

As shown in FIG. 7, the input pins may include pins for receiving signals, such as the external clock signal CLK 602, ECG signals ECG_DATA 702, and the chip enable signal CE 610. Further, the input pins also include pins for receiving signals for a highest power supply VCC (not shown) and for a lowest power supply GND (not shown). In an implementation, the highest power supply may be a voltage in a range of 0.6 V to 1.2 V, and the lowest power supply a voltage of 0 V. The choice of voltages may vary based on the application of the cardiovascular disease detection apparatus 200.

Further, as shown in FIG. 7, signals such as the CLK 602, the ECG_DATA 702, the CE 610, and the CLK_CHIP 612 may be provided from the clock generator 204 to the QRS identification system 206. In one implementation, as shown in FIG. 7, the output pins may include pins for drawing out signals, such as a beat to beat interval signal RR 704, a signal from where serial output to be captured PISO 706, an R wave peak value signal R_PEAK 708, a Q wave peak value signal Q_PEAK 710, an S wave peak value signal SPEAK 712, an R prime value peak signal Rp_PEAK 714, a QRS duration signal QRSD 716, and a signal for indicating larger S wave duration than R wave SGRTR 718. In one implementation, the signal being drawn out of the output pins may be provided to the disease detector 208 of the cardiovascular disease detection apparatus 200.

In one implementation, the RR 704 is indicative of a time interval between the occurrences of two consecutive R peaks. The PISO 706 is indicative of availability of signals at the output pins. The PISO 706 signal may be checked to determine that remaining output signals are available without any obstruction. Further, the R_PEAK 708 is indicative of the R peak of the R wave of the QRS complex 500. Similarly, the Q_PEAK 710 and the S_PEAK 712 are indicative of the Q peak of the Q wave and the S peak of the S wave of the QRS complex 500, respectively. Further, the Rp_Peak 714 is indicative of a peak value of a secondary R wave, in case a secondary R wave is obtained along with the R peak of the QRS complex 500. The QRSD 716 is indicative of a time duration of the occurrence of the QRS complex 500 as identified earlier. The SGRTR 718 is indicative of a time duration of the S wave being larger than a time duration of the R wave.

In one implementation, the cardiovascular disease detection apparatus 200 may be operated in a plurality of operational modes depending on the signals at the input pins of the clock generator 204. The plurality of operational modes may include, but are not limited to, a Reset mode and a Normal mode.

Table 1 illustrates operating conditions of the cardiovascular disease detection apparatus 200 for each of the plurality of operational modes. The operating condition refers to a combination of signals, such as CE 610, and CLK 602. The combinations of signals in Table 1 are for the purpose of explanation and are by no means restricted to the examples as the mentioned herein.

TABLE 1

| CE | CLK | Operation |
|----|-----|-----------|
| 1  | X   | RESET     |
| 0  | 1   | Normal Mode |

In an implementation, initially, the cardiovascular disease detection apparatus 200 may be operated in the reset mode. In the reset mode, the components of the clock generator 204 and the QRS identification system 206 are initialized to a logic 0. Once the components are initialized to the logic 0, the cardiovascular disease detection apparatus 200 may be operated in the normal mode. The normal mode is indicative of an operational mode when the ECG signal, captured by the ECG recorder 202, may be forwarded to the QRS identification system 206 for identification of QRS complexes.

As can be seen from Table 1, in order to put the cardiovascular disease detection apparatus 200 in the reset mode, a high signal is provided through the CE pin 610. Irrespective of the signals being provided to the CLK pin 602, once the CE pin 610 receives the high signal, the cardiovascular disease detection apparatus 200 may enter the reset mode. Further, in order to put the cardiovascular disease detection apparatus 200 in the normal mode, a high signal is provided to the CLK pin 602, and a low signal is provided to the CE pin 610. In one implementation, the output signals may be utilized for detection of cardiovascular diseases.

Figure 8:
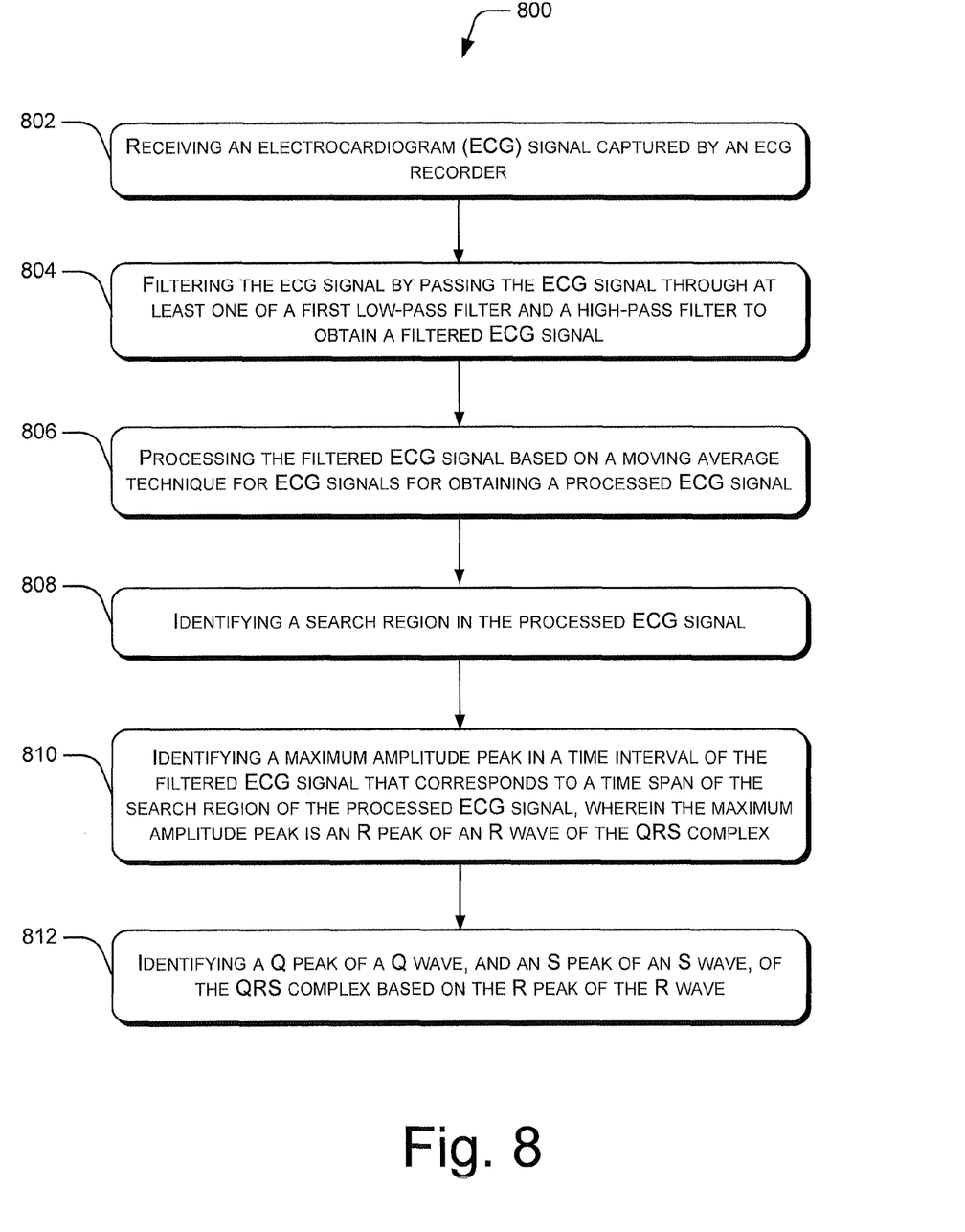
FIG. 8 illustrates a method for identification of QRS complexes in Electrocardiograms (ECG) signals, in accordance with an embodiment of the present subject matter.

FIG. 8 illustrates a method for identification of QRS complexes in Electrocardiograms (ECG) signals for detection of cardiovascular diseases, in accordance with an embodiment of the present subject matter. The method 800 may be implemented in a variety of computing systems in several different ways. For example, the method 800, described herein, may be implemented in the QRS identification system 206, and in the cardiovascular disease detection apparatus 200, as described above.

The order in which the method 800 are described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the methods can be implemented in any suitable hardware, software, firmware, or combination thereof. It will be understood that even though the method 800 are described with reference to the system 206, the description may be extended to other systems as well.

With reference to the description of FIG. 8, for the sake of brevity, the details of the components of the QRS identification system 206 are not discussed here. Such details can be understood as provided in the description provided with reference to FIGS. 2, 3, 4, 5, 6 and 7.

The method 800 may facilitate identification of QRS complexes in ECG signals for detection of cardiovascular diseases. At block 802, an ECG signal captured by an ECG recorder, may be received. In one implementation, a signal receiving block 304 of the QRS identification system 206 may receive the ECG signal, as explained earlier.

Once the ECG signal may be received, at block 804, the ECG signal may be filtered by passing the ECG signal through at least one of a first low-pass filter and a high-pass filter to obtain a filtered ECG signal. The ECG signal may be passed through at least one of the first low-pass filter and the high-pass filter in order to obtain a noise-free filtered ECG signal. In one implementation, the signal receiving block 304 of the QRS identification system 206 may pass the ECG signal through at least one of the first low-pass filter and the high-pass filter, as explained earlier. In one implementation, the first low-pass filter and the high-pass filter may have a cut-off frequency within a range of 15 Hz-40 Hz and 0.5 Hz-5 Hz, respectively.

At block 806, the filtered ECG signal may further be processed, based on a moving average technique for ECG signals, for obtaining a processed ECG signal. In one implementation, the processing of the filtered ECG signal may further include squaring the filtered ECG signal to obtain a squared filtered ECG signal. Further, peaks of the squared filtered ECG signal may be captured for generating an envelope ECG signal. The envelope ECG signal is a signal that envelops the peaks of the filtered ECG signal. Subsequently, a moving average ECG signal may be determined based on a moving average of sample points associated with the envelope ECG signal. In one implementation, the moving average ECG signal may be passed through a second low-pass filter to obtain the processed ECG signal. In one implementation, the second low-pass filter may have a cut-off frequency within a range of 8 Hz-16 Hz. In one implementation, the signal processing block 306 of the QRS identification system 206 may process the filtered ECG signal based on a moving average technique for ECG signals, for obtaining the processed ECG signal, as explained earlier.

After generating the processed ECG signal, at block 808, a search region may be identified in the processed ECG signal. The search region is indicative of a time span between two consecutive peaks of the processed ECG signal. In one implementation, the peaks of the processed ECG signal, to be utilized for detection of the search regions, may be detected on a peak threshold. In one implementation, the QRS identification block 308 of the QRS identification system 206 may identify the search region in the processed ECG signal, as explained earlier.

Subsequently, at block 810, a maximum amplitude peak may be identified in a time interval of the filtered ECG signal that corresponds to the time span of the search region of the processed ECG signal. In one implementation, the maximum amplitude peak is an R peak of an R wave of the QRS complex. In one implementation, the QRS identification block 308 of the QRS identification system 206 may identify the maximum amplitude peak in the time interval of the filtered ECG signal, as explained earlier.

At block 812, a Q peak of a Q wave, and an S peak of an S wave, of the QRS complex may be identified based on the R peak of the R wave. In one implementation, the QRS identification block 308 of the QRS identification system 206 may identify the Q peak and the S peak of the QRS complex, as explained earlier.

Although implementations of a method for identification of QRS complexes in ECG signals have been described in language specific to structural features and/or methods, it is to be understood that the present subject matter is not necessarily limited to the specific features or methods described.

We claim:

1. A method for identifying a QRS complex in an Electrocardiogram (ECG) signal, the method comprising:
   receiving the ECG signal captured by an ECG recorder, wherein the ECG signal is indicative of an electrical activity of heart of an individual;
   filtering the ECG signal by passing the ECG signal through at least one of a first low-pass filter and a high-pass filter to obtain a filtered ECG signal;
   squaring the filtered ECG signal to obtain a squared filtered ECG signal;
   generating an envelope ECG signal by capturing peaks of the squared filtered ECG signal;
   determining a moving average ECG signal based on a moving average of sample points associated with the envelope ECG signal, wherein a sample point is indicative of an amplitude of the envelope ECG signal at a time instance; and
   filtering the moving average ECG signal to obtain a processed ECG signal, by passing the moving average ECG signal through a second low-pass filter;
   identifying a search region in the processed ECG signal, wherein the search region is indicative of a time span between two consecutive peaks of the processed ECG signal;
   identifying a maximum amplitude peak in a time interval of the filtered ECG signal that corresponds to the time span of the search region of the processed ECG signal, wherein the maximum amplitude peak is an R peak of an R wave of the QRS complex; and
   identifying a Q peak of a Q wave, and an S peak of an S wave, of the QRS complex based on the R peak of the R wave.

2. The method as claimed in claim 1 further comprising down-sampling the ECG signal for passing the sampled ECG signal through the at least one of the first low-pass filter and the high-pass filter, wherein the ECG signal is down-sampled based on a predefined reduction factor.

3. The method as claimed in claim 1, wherein the identifying the Q peak of the Q wave of the QRS complex comprises:
   identifying a first sub-search region of the filtered ECG signal, wherein the first sub-search region is a region comprising a predefined set of sample points of the filtered ECG signal before a time instance of the R peak;
   determining a first peak point in a segment of the filtered ECG signal, within the first sub-search region, wherein the segment comprises a predefined number of consecutive sample points with slope greater than a predefined slope threshold, and wherein the first peak point is one of the predefined number of consecutive sample points in the segment;
   determining a second peak point that corresponds to a peak of the filtered ECG signal in the first sub-search region, wherein the second peak point is determined as a zero crossing point of a slope signal, wherein the slope signal is obtained from three-point derivatives of filtered ECG signal in the first sub-search region; and wherein the Q peak of the Q wave of the QRS complex is identified as one of the first peak point and the second peak point which is closer to the R peak of the R wave of the QRS complex.

4. The method as claimed in claim 3, further comprising determining a third peak point of the filtered ECG signal, based on a minimum value of the filtered ECG signal in the first sub-search region, when the first peak point and the second peak point are not determined, wherein the Q peak of the Q wave of the QRS complex is identified as the third peak point.

5. The method as claimed in claim 1, wherein the identifying the S peak of the S wave of the QRS complex comprises:
identifying a second sub-search region of the filtered ECG signal, wherein the second sub-search region is a region comprising a predefined set of sample points of the filtered ECG signal after a time instance of the R peak;
determining a first peak point in a segment of the filtered ECG signal, within the second sub-search region, wherein the segment comprises a predefined number of consecutive sample points with slope greater than a predefined slope threshold, and wherein the first peak point is one of the predefined number of consecutive sample points in the segment;
determining a second peak point that corresponds to a peak of the filtered ECG signal in the second sub-search region, wherein the second peak point is determined as a zero crossing point of a slope signal, wherein the slope signal is obtained from three-point derivatives of filtered ECG signal in the second sub-search region; and
wherein the S peak of the S wave of the QRS complex is identified as one of the first peak point and the second peak point which is closer to the R peak of the R wave of the QRS complex.

6. The method as claimed in claim 5, further comprising determining a third peak point of the filtered ECG signal, based on a minimum value of the filtered ECG signal in the second sub-search region, when the first peak point and the second peak point are not determined, wherein the S peak of the S wave of the QRS complex is identified as the third peak point.

7. A QRS identification system for identifying a QRS complex in an Electrocardiogram (ECG) signal, the QRS identification system comprising:
a processing unit;
a signal receiving block, coupled to the processing unit, to receive the ECG signal captured by an ECG recorder, wherein the ECG signal is indicative of an electrical activity of heart of an individual; and
filter the ECG signal by passing the ECG signal through at least one of a first low-pass filter and a high-pass filter to obtain a filtered ECG signal;
a signal processing block, coupled to the processing unit, to square the filtered ECG signal to obtain a squared filtered ECG signal;
generate an envelope ECG signal by capturing peaks of the squared filtered ECG Signal;
determine a moving average ECG signal based on a moving average of sample points associated with the envelope ECG signal, wherein a sample point is indicative of an amplitude of the envelope ECG signal at a time instance; and
filter the moving average ECG signal to obtain a processed ECG signal, by passing the moving average ECG signal through a second low-pass filter; and a QRS identification block, coupled to the processing unit, to determine a search region in the processed ECG signal, wherein the search region is indicative of a time span between two consecutive peaks of the processed ECG signal;
detect a maximum amplitude peak in a time interval of the filtered ECG signal that corresponds to the time span of the search region of the processed ECG signal, wherein the maximum amplitude peak is an R peak of an R wave of the QRS complex; and
identify a Q peak of a Q wave and an S peak of an S wave of the QRS complex, based on the R peak of the R wave.

8. The QRS identification system as claimed in claim 7, wherein the signal receiving block is coupled to the processing unit to down-sample the ECG signal for passing the sampled ECG signal through the at least one of the first low-pass filter and the high-pass filter, wherein the ECG signal is down-sampled based on a predefined reduction factor.

9. The QRS identification system as claimed in claim 7, wherein the QRS identification block is coupled to the processing unit to identify the two consecutive peaks of the processed ECG signal, for the determination of the search region, based on a peak threshold, the two consecutive peaks being indicative of peaks with an amplitude above the peak threshold.

10. The QRS identification system as claimed in claim 9, wherein the QRS identification block is coupled to the processing unit to determine the peak threshold for a predefined number of search regions, based on average of peaks occurred in a previous set of the predefined number of search regions.

11. The QRS identification system as claimed in claim 7, wherein the QRS identification block is coupled to the processing unit to,
identify a first sub-search region of the filtered ECG signal, wherein the first sub-search region is a region comprising a predefined set of sample points of the filtered ECG signal before a time instance of the R peak;
determine a first peak point in a segment of the filtered ECG signal, within the first sub-search region, wherein the segment comprises a predefined number of consecutive sample points with slope greater than a predefined slope threshold, and wherein the first peak point is one of the predefined number of consecutive sample points in the segment; and
determine a second peak point that corresponds to a peak of the filtered ECG signal in the first sub-search region, wherein the second peak point is determined as a zero crossing point of a slope signal, wherein the slope signal is obtained from three-point derivatives of filtered ECG signal in the first sub-search region;
wherein the Q peak of the Q wave of the QRS complex is identified as one of the first peak point and the second peak point which is closer to the R peak of the R wave of the QRS complex.

12. The QRS identification system as claimed in claim 11, wherein the QRS identification block is coupled to the processing unit to
determine a third peak point of the filtered ECG signal, based on a minimum value of the filtered ECG signal in the first sub-search region, when the first peak point and the second peak point are not determined, wherein the Q peak of the Q wave of the QRS complex is identified as the third peak point.

13. The QRS identification system as claimed in claim 7, wherein the QRS identification block is coupled to the processing unit to identify a second sub-search region of the filtered ECG signal, wherein the second sub-search region is a region comprising a predefined set of sample points of the filtered ECG signal after a time instance of the R peak;

determine a first peak point in a segment of the filtered ECG signal, within the second sub-search region, wherein the segment comprises a predefined number of consecutive sample points with slope greater than a predefined slope threshold, and wherein the first peak point is one of the predefined number of consecutive sample points in the segment;

determine a second peak point that corresponds to a peak of the filtered ECG signal in the second sub-search region, wherein the second peak point is determined as a zero crossing point of a slope signal, wherein the slope signal is obtained from three-point derivatives of filtered ECG signal in the first sub-search region; and wherein the S peak of the S wave of the QRS complex is identified as one of the first peak point and the second peak point which is closer to the R peak of the R wave of the QRS complex.

14. The QRS identification system as claimed in claim 13, wherein the QRS identification block is coupled to the processing unit to determining a third peak point of the filtered ECG signal, based on a minimum value of the filtered ECG signal in the second sub-search region, when the first peak point and the second peak point are not determined, wherein the S peak of the S wave of the QRS complex is identified as the third peak point.

15. The QRS identification system as claimed in claim 7, wherein the first low-pass filter has a cut-off frequency within a range of 15 Hz-40 Hz, and wherein the high-pass filter has a cut-off frequency within a range of 0.5 Hz-5 Hz, and wherein the second low-pass filter has a cut-off frequency within a range of 8 Hz-16 Hz.

16. A cardiovascular disease detection apparatus for detection of cardiovascular diseases using QRS complex in Electrocardiogram (ECG) signals, the cardiovascular disease detection apparatus comprising:

a clock generator;

an ECG recorder, coupled to the clock generator, to record an ECG signal, the ECG signal being indicative of an electrical activity of heart of an individual; and a QRS identification system, coupled to the clock generator, to receive the ECG signal captured by the ECG recorder;

filter the ECG signal by passing the ECG signal through at least one of a first low-pass filter and a high-pass filter to obtain a filtered ECG signal;

square the filtered ECG signal to obtain a squared filtered ECG signal;

generate an envelope ECG signal by capturing peaks of the squared filtered ECG signal;

determine a moving average ECG signal based on a moving average of sample points associated with the envelope ECG signal, wherein a sample point is indicative of an amplitude of the envelope ECG signal in a time-amplitude curve at a time instance; and filter the moving average ECG signal to obtain a processed ECG signal, by passing the moving average ECG signal through a second low-pass filter;

identify a search region in the processed ECG signal, wherein the search region is indicative of a time span between two consecutive peaks of the processed ECG signal;

identify a maximum amplitude peak in a time interval of the filtered ECG signal that corresponds to the time span of the search region of the processed ECG signal, wherein the maximum amplitude peak is an R peak of an R wave of the QRS complex; and identify a Q peak of a Q wave and an S peak of an S wave of the QRS complex, based on the R peak of the R wave; and a disease detector for detecting a cardiovascular disease based on the QRS complex of the ECG signal.

17. The cardiovascular disease detection apparatus as claimed in claim 16, wherein the clock generator comprises:

a device to, receive an external clock signal (CLK); and generate an inverted clock signal (CLKB), based on the external clock signal (CLK); and a counter to receive the inverted clock signal (CLKB) and a chip enabled signal (CE), wherein a high chip enabled signal (CE) is provided to reset the counter; and generate an internal generated signal (CLK_CHIP), based on the external clock signal, wherein the internal generated clock signal (CLK_CHIP) is a fraction of the external clock signal.

* * * * *